(12) United States Patent
Vicente

(10) Patent No.: US 8,465,097 B2
(45) Date of Patent: Jun. 18, 2013

(54) MEDICAL SUPPORT SYSTEM

(76) Inventor: Antonio Vicente, Malden, MA (US)

( * ) Notice: Subject to any disclaimer, the term of this patent is extended or adjusted under 35 U.S.C. 154(b) by 298 days.

(21) Appl. No.: 12/898,699

(22) Filed: Oct. 5, 2010

(65) Prior Publication Data

US 2012/0080921 A1    Apr. 5, 2012

(51) Int. Cl.
*A47C 7/36* (2006.01)
*A61G 15/00* (2006.01)

(52) U.S. Cl.
USPC ............................................ 297/391; 297/405

(58) Field of Classification Search
USPC ............................ 297/391, 397, 405, 406, 407
See application file for complete search history.

(56) References Cited

U.S. PATENT DOCUMENTS

| | | | | |
|---|---|---|---|---|
| 461,928 A * | 10/1891 | White | | 297/115 |
| 866,753 A * | 9/1907 | Weber | | 297/405 |
| 3,216,767 A * | 11/1965 | Lutfy | | 297/391 |
| 5,927,815 A * | 7/1999 | Nakamura et al. | | 297/411.38 |
| 6,594,839 B1 * | 7/2003 | Papay | | 5/637 |
| 6,682,143 B2 * | 1/2004 | Amirault et al. | | 297/250.1 |
| 7,631,935 B2 * | 12/2009 | Chen et al. | | 297/284.9 |

* cited by examiner

*Primary Examiner* — Sarah B McPartlin
(74) *Attorney, Agent, or Firm* — Arnold de Guzman

(57) ABSTRACT

A medical support system for medical professionals performing procedures on patients. That medical support system includes adjustable support arms adjacent a patient headrest. The support arms are padded, have concave support surfaces, can freely rotate and pivot, but can also be locked in position via a ball-joint mechanism inside a housing. The ball joint has a compression cap with a conically shaped opening that aligns with a ball that receives a rod that connects to a support arm. Turning the compression cap induces a state of snugness achieved by friction between the ball, the compression cap and the housing. Loosening the compression cap allows rotational and angular positioning of the support arms. The compression cap has a knurled outer surface to assist a medical professional using the medical support system.

20 Claims, 6 Drawing Sheets

MEDICAL SUPPORT SYSTEM

FIELD OF THE INVENTION

The present invention relates to medical devices. More particularly, the present invention relates to medical devices that support medical professionals performing procedures on patients seated on a medical chair.

BACKGROUND OF THE INVENTION

During many medical procedures patients sit on chairs having headrests. For example, patients receiving dental, plastic surgery, eye care, or dermatology care often sit for prolonged periods of time on special medical chairs that are designed not only for patient comfort but also to properly position them for an attending medical professional.

While such special medical chairs have proven successful in providing comfort and support for patients, they rarely provide support for the attending medical professional. This can cause medical professionals to suffer back, shoulder, and arm pain as well as other discomforts during and after lengthy medical procedures. Such discomforts can lead to an increased likelihood of mistakes as well as serious short and long term problems for the medical professional.

Accordingly, there remains a need for a system that provides medical professionals with support when they are performing medical procedures on patients sitting in a medical chair.

SUMMARY

According to one aspect of the disclosed subject matter there is provided a medical support system for medical professionals when they are performing procedures on patients sitting on a medical chair. That medical support system includes highly adjustable support arms located adjacent a patient headrest. The support arms are beneficially padded and have concave support surfaces. The support arms can rotate and pivot, but can also be rigidly locked into position. By combining positional and rotational adjustments, and by using the concave outer surfaces, the support arms can be adjusted to enable a medical professional to properly position the support arms relative to a patient in the medical chair while also providing the medical professional with comfort and support.

Positioning and locking are enabled via a ball-joint mechanism located inside a housing. The ball joint is locked using a compression cap having a conically shaped opening that aligns with a ball that receives a rod that connects to a support arm. The shaped opening allows the support arms to pivot and rotate. Turning the compression cap induces a state of snugness achieved by friction between the ball, the compression cap and the housing. Loosening the compression cap allows simultaneous rotational and angular positioning of the support arms. Subsequent tightening of the compression cap firmly locks the ball, and thus the support arm, in position. Beneficially, the compression cap has a knurled outer surface to assist adjust by a medical professional. The medical support system attaches to the medical chair, beneficially via an attachment arm/slot configuration.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Further, the claimed subject matter is not limited to implementations that solve any or all disadvantages noted in any part of this disclosure.

BRIEF DESCRIPTION OF THE DRAWINGS

The advantages and features of the present invention will become better understood with reference to the following detailed description and claims when taken in conjunction with the accompanying drawings, in which like elements are identified with like symbols, and in which:

It should be noted that the terms "a" and "an" used herein do not denote a limitation of quantity, but rather denote the presence of at least one of the referenced items.

DETAILED DESCRIPTION OF THE INVENTION

While the principals of the present invention are explained herein with reference to FIGS. 1 through 3B, it should be understood that the present invention is not limited to the specifically described and illustrated embodiment. A person skilled in the art will appreciate that many other embodiments of the invention are possible without deviating from the basic concept of the invention as defined by the appended claims.

The principles of the present invention enable a medical chair and a medical support system that provides support for medical professionals such as dentists, ophthalmologists, and dental hygienist when they are performing medical services on a patient. The medical support system is highly adjustable yet provides rigid support.

Figure 1:
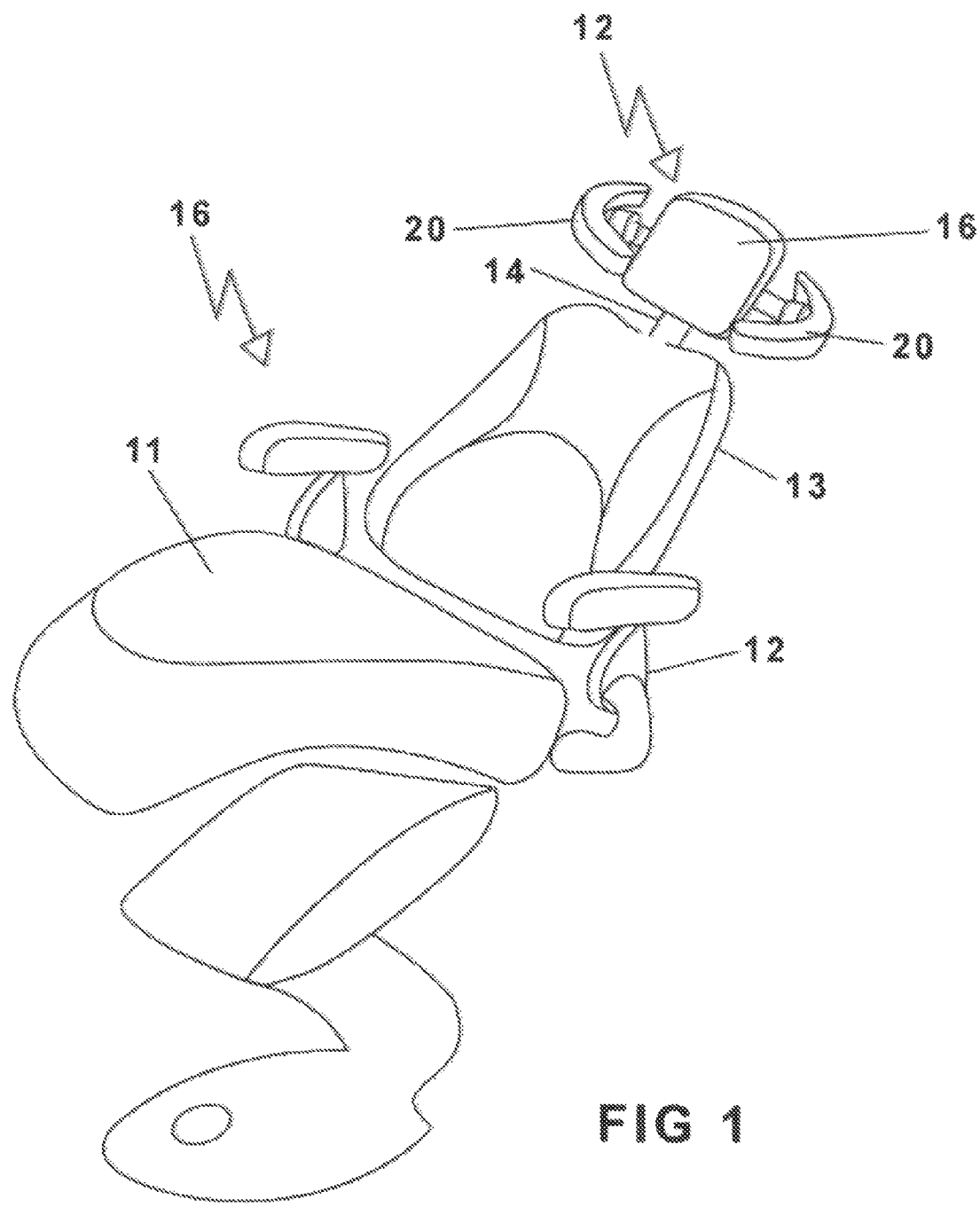
FIG. 1 is a perspective view of a medical chair 10 along with a medical support system 12 that is in accord with the principals of the present invention.

FIG. 1 illustrates a typical medical chair 10 and medical support system 12 suitable for incorporating the principles of the present invention. The medical chair 10 includes patient support surfaces 11 for receiving and supporting a patient firmly yet comfortably. The medical chair 10 itself would usually be highly adjustable to enable positioning a patient in the proper position to undergo a medical position. For example the medical chair might rotate along a vertical axis, might raise and lower a patient as required, and might include arm, leg, and lumbar support. In any event the medical chair includes a back support 13.

Still referring to FIG. 1, attached to the back support 13 is the medical support system 12 which extends from the medical chair 10 via an adjustable attachment arm 14 (subsequently described in more detail). The attachment arm 14 enables the medical support system 12 to be adjusted to properly fit a patient sitting in the medical chair 10 while also providing support for a medical professional.

For patient comfort the medical support system 12 includes a padded cushion 16 that supports and comforts a patient's head. The padded cushion 16 is placed over a rear mounting plate 18 (see FIGS. 2B and 3B) that also connects to the attachment arm 14 (FIG. 3B). The attachment arm 14 and the mounting plate 18 enable the required rigidity of the medical chair 10-medical support system 12 combination. While the attachment arm 14 and the mounting plate 18 have been described as being two different elements it is obviously possible to use a single element to perform both functions. However, if different elements are used the attachment arm 14 and the mount plate 18 can be connected together using common fasteners such as threaded fasteners, rivets, or welding/chemical bonding techniques.

Figure 2A:
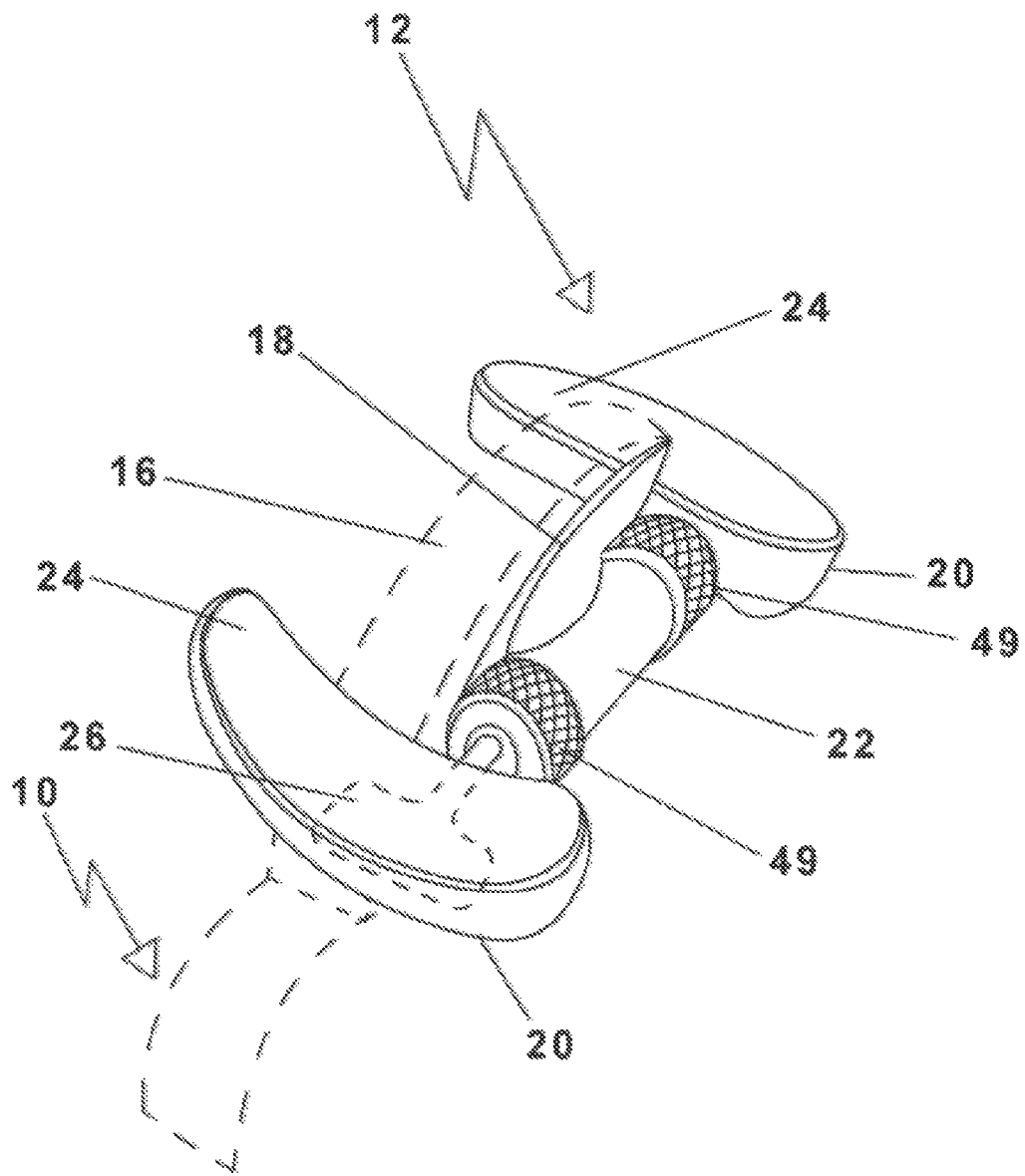
FIG. 2A is another perspective view of the medical chair 10 and the medical support system 12 illustrated in FIG. 1.

Referring now to both FIGS. 1 and 2A, the medical support system 12 includes support arms 20 that extend from the remainder of the medical support system 12. As the support arms 20 are used to support a medical professional that is providing medical care to a patent sitting in the medical chair 10, the support arms 20 can be rigidly fixed relative to the medical chair 10. Furthermore, the support arms 20 are adjustable to enable the medical professional to perform the medical procedure. How the medical support system 12 achieves both rigidity and adjustability for the support arms 20 is described subsequently.

Referring now specifically to FIG. 2A, the support arms 20 extend from an elongated housing 22 that is rigidly attached to the mounting plate 18. The support arms 20 are beneficially configured to have concave outer surfaces 24. As the support arms 20 are fully rotatable and pivotal (see below) the concave outer surfaces may open upwards, downwards, or in a wide range of other directions.

Figure 2B:
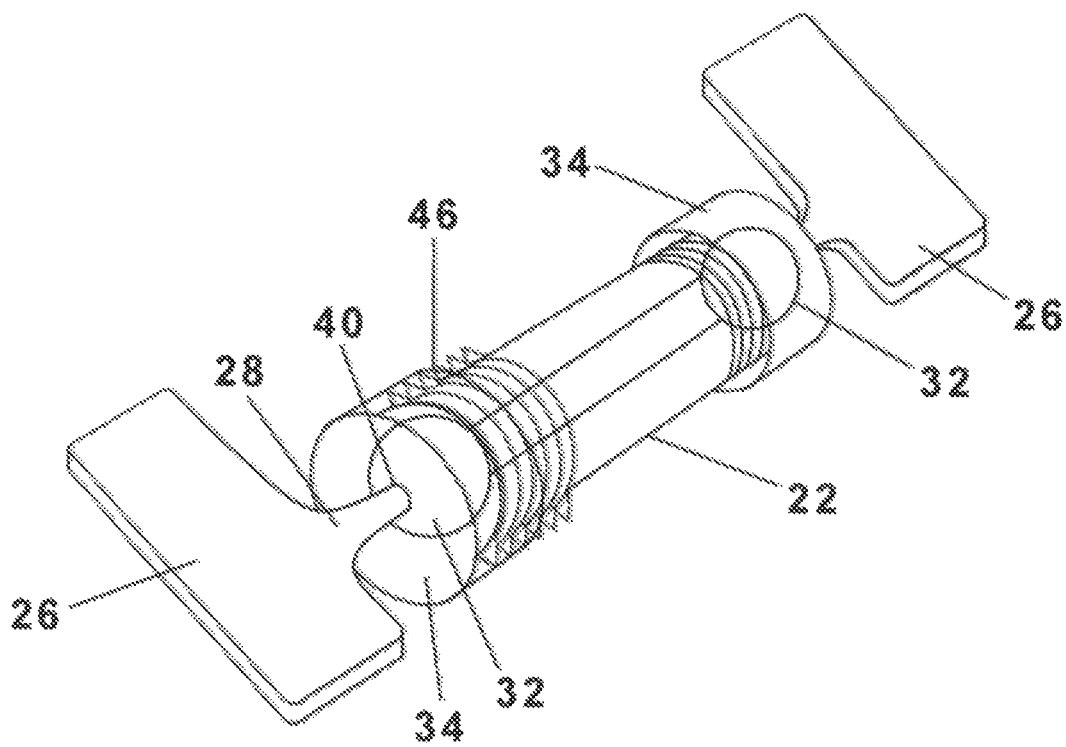
FIG. 2B is a perspective view that primarily illustrates the medical support system 12 illustrated in FIGS. 1 and 2A in more detail.
Figure 2C:
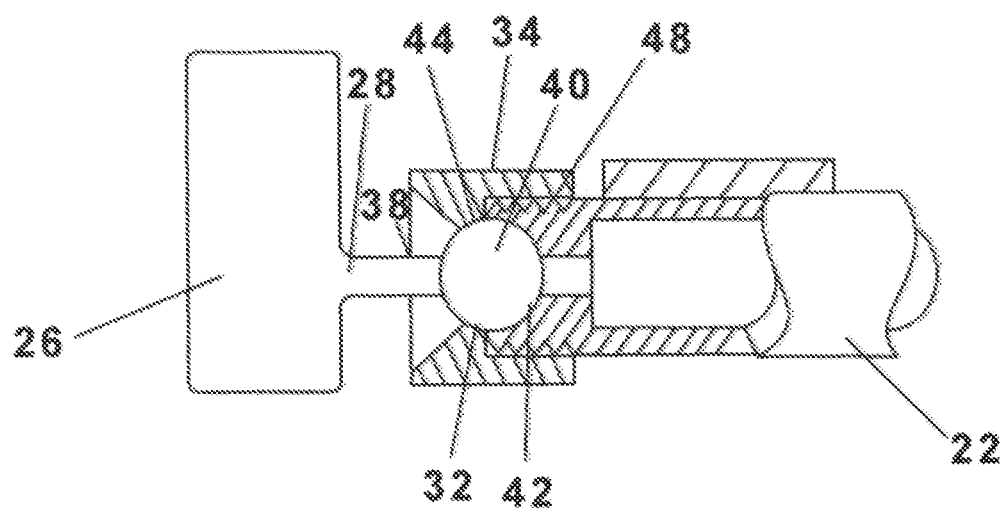
FIG. 2C is a partial sectional view of the medical support system 12.

The support arms 20 are formed by adding padding to a core 26 on the end of an elongated rod 28 (which is best shown in FIGS. 2B and 2C). As described in more detail subsequently, the support arms 20 can be rotated and positioned about the housing 22. By combining positional and rotational adjustments, and by using the concave outer surfaces 24, the support arms 20 can be adjusted to enable a medical professional to properly position the support arms 20 relative to a patient in the medical chair 10 while also providing the medical professional with both comfort and support.

To provide the required rigidity and adjustability the housing 22 includes locking features for selectively locking the support arms 20 in their desired positions. That locking feature is described with reference to FIGS. 2B and 2C. Inside each end of the housing 22 is a ball 32 which is retained inside the housing 22 by a compression cap 34. The body of each compression cap 34 forms a conically shaped opening 38 which aligns with a ball 32. Each ball 32 receives a rod 28 of a support arm 20. The rod 28 is rigidly attached to the ball 32 (achieved using threaded screws, chemical bonding, welding, or another standard fastening mechanism). Furthermore, each ball 32 fits into a cup defined by a housing seat 42 that is formed in the body of the housing 22 and a cap seat 44 that is formed in the body of the compression cap 34. The end of the housing 22 has outer threads 46 that mate with internal threads 48 of the compression cap 34. This forms a cap-screw assembly. Thus the ball 32 is captured herebetween the cap seat 44 and the housing seat 42, thereby forming a ball joint mechanism.

Rotating the compression cap 34 clockwise induces a state of snugness achieved by friction between the ball 32, the cap seat 44 and the housing seat 42. Loosening the compression cap 34 allows simultaneous pivotal and angular positioning of the support arms 20 to a desired user-friendly position. Subsequent tightening of the compression cap 34 firmly locks the ball 32 between the cap seat 44 and the housing seat 42, thereby locking a support arm 20 in position. To assist a medical professional to loosen and tighten the compression cap 34 that cap beneficially includes a knurled outer surface 49 (shown in FIGS. 2A and 3B).

Figure 3A:
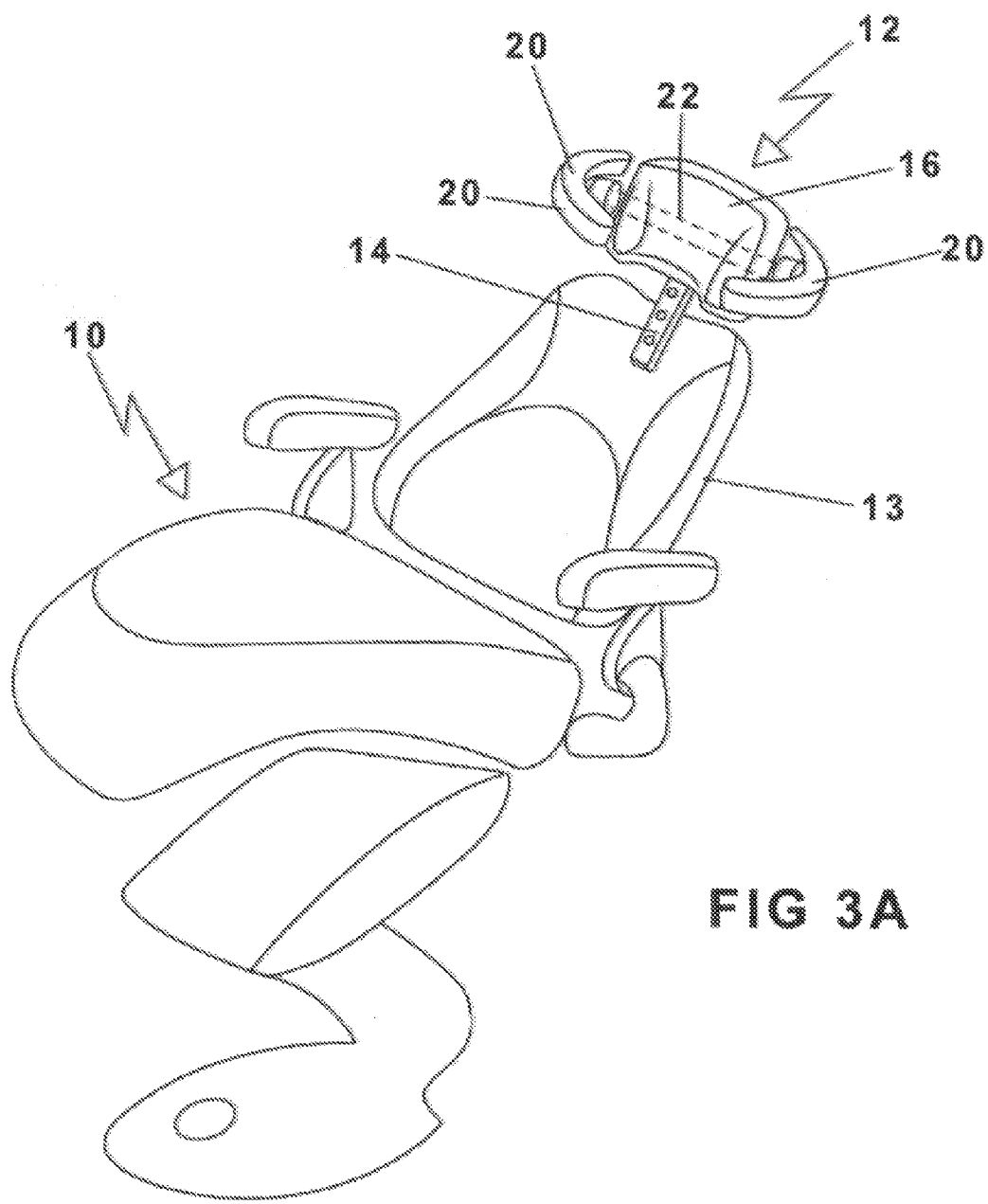
FIG. 3A is a perspective and partial sectional view that highlights the connection of the medical support system 12 to the medical chair 10.
Figure 3B:
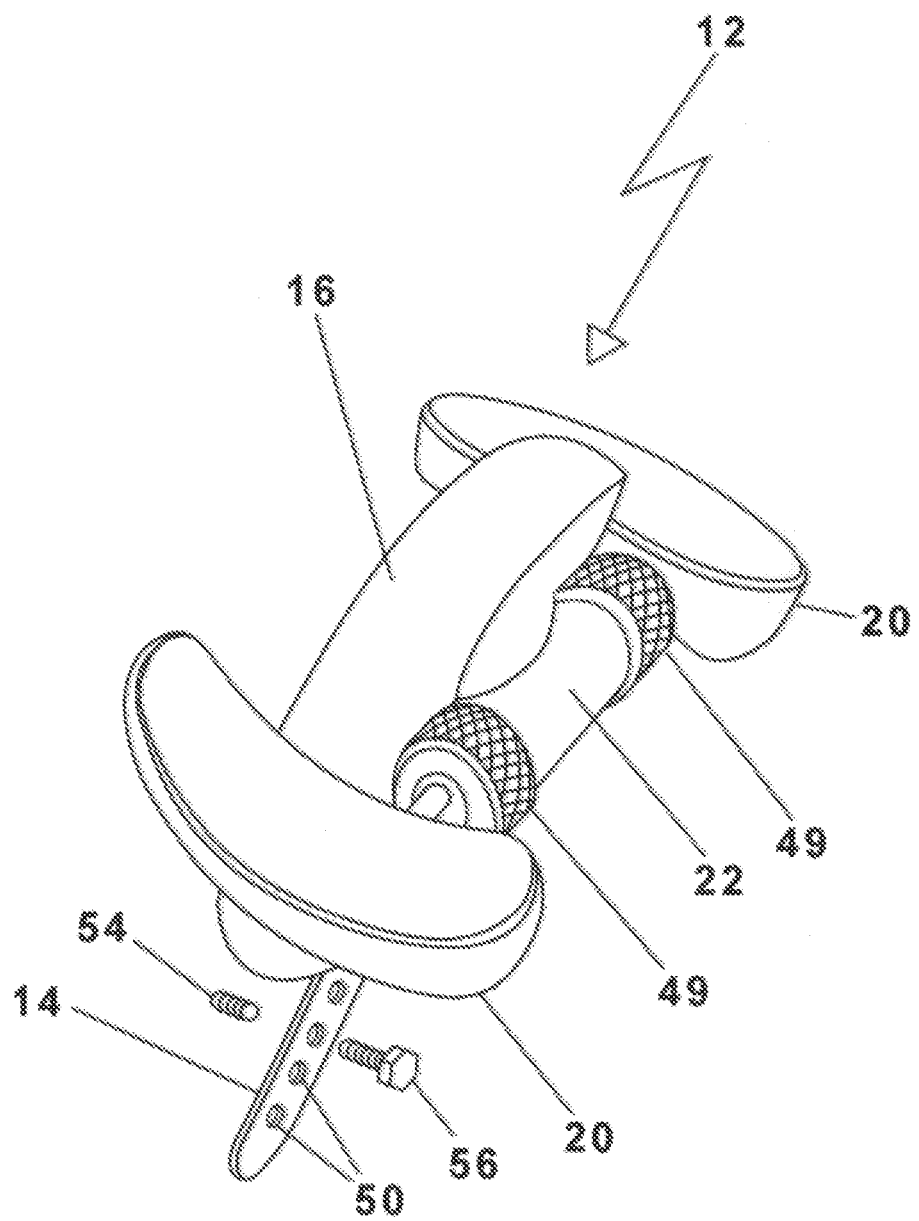
FIG. 3B is a perspective view that shows the lower part of the medical support system 12.

The medical support system 12 must be attached to the medical chair 10. FIGS. 3A and 3B illustrate a preferred method of performing that attachment. The attachment arm 14 (referenced above) is formed as an elongated element having a series of adjustment holes 50. The attachment arm 14 slides into a slot 52 within the back support 13. The back support 13 includes a threaded nut 54 adjacent the slot 52. As the attachment arm 14 is fit into the slot 52 the various adjustment holes 50 selectively align with the threaded nut 54. When the medical support 12 is properly positioned a screw 56 passes through an adjustment hole 50 and into the threaded nut 54. When the screw 56 is tightened into the threaded nut 54 the attachment arm 14 is rigidly fastened into place in the slot 52.

While the attachment arm 14 is illustrated as a single flat element with adjustment holes 50 this is certainly not a requirement. For example, multiple flat elements, or one or more rods or bars are also possible attachment elements. Furthermore, the medical support 12 and the medical chair 10 can be joined in completely different manners. For example, the attachment arm 14 might be a threaded element configured to fit into a threaded portion of the medical chair 10, or a tongue-and-groove configured support/chair system might be used. Indeed, the medical support 12 might be an integral part of the medical chair 10. In any event, after initial purchase or acquisition the medical support 12 would beneficially be usable by the common user in a simple and effortless manner with little or no training.

The attachment arm 14, the mounting plate 18, the support arms 20, the housing 22, the core 26, the rods 28, the compression caps 34, and the balls 32 are beneficially comprised of materials capable of rigidly supporting a medical professional when that professional is performing medical procedures on a patient sitting in the medical chair 10. Such materials include, but are not limited to polymeric or acrylic plastics, aluminum, steel, stainless steel, brass, carbon fiber composites, fiber glass, or plastic coated steel. The support arms 20 are beneficially ergonomically shaped, foam padded, and plastic covered.

It is envisioned that other styles and configurations of the present invention can be easily incorporated into the teachings of the present invention, and only one particular configuration shall be shown and described for purposes of clarity and disclosure and not by way of limitation of scope.

The foregoing description of an embodiment of the present invention has been presented for purposes of illustration and description. It is not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated

What is claimed is:

1. A medical support system, comprising:
a mounting support;
a head rest having a mounting plate, said mounting plate being rigidly attached to the mounting support;
a support arm adjacent said head rest and attached to said mounting support, said support arm including support surfaces;
wherein said mounting support comprises a housing;
wherein said support arm comprises an elongated rod and a ball, wherein the rod is rigidly attached to the ball, wherein said rod and ball form a ball-joint mechanism, and wherein the support surface is attached to the rod;

wherein the ball is retained inside the housing;

wherein said support arm is selectively pivotal and rotatable; and wherein said support arm can selectively be locked in position.

2. The medical support system of claim 1, wherein said support surfaces include a padded surface.

3. The medical support system of claim 2, wherein said padded surface has a concave shape.

4. The medical support system of claim 1, wherein said support arm is attached to said mounting support using the ball-joint mechanism.

5. The medical support system of claim 4, wherein said ball-joint mechanism includes the ball within a cup inside the housing.

6. The medical support system of claim 5, wherein said cup is formed by a compression cap having a cap seat and by a housing seat, wherein said cap seat and said housing seat are configured to contact said ball.

7. The medical support system of claim 6, wherein said compression cap and said housing are threaded to form a cap screw assembly.

8. The medical support system of claim 7:

wherein said ball connects to the rod that passes through said compression cap, said rod connecting to said mounting support;

wherein said compression cap has a conically shaped opening that receives said rod;

wherein when said cap-screw assembly is loose said rod can pivot and rotate; and wherein when said cap-screw assembly is tightened said rod is locked in position.

9. The medical support system of claim 6, wherein said compression cap has a knurled outer surface.

10. The medical support system of claim 6, wherein said medical support system includes a means for attachment to a medical chair.

11. A medical chair having a medical support system, comprising:

a mounting support;

a head rest having a mounting plate, said mounting plate being rigidly attached to the mounting support;

a support arm adjacent said head rest and attached to said mounting support, said support arm including support surfaces;

wherein said mounting support comprises a housing;

wherein said support arm comprises an elongated rod and a ball, wherein the rod is rigidly attached to the ball, wherein said rod and ball form a ball-joint mechanism, and wherein the support surface is attached to the rod;

wherein the ball is retained inside the housing;

wherein said support arm is selectively pivotal and rotatable; and wherein said support arm can selectively be locked in position.

12. The medical chair of claim 11, wherein said support arm includes a padded surface.

13. The medical chair of claim 12, wherein said padded surface is concave.

14. The medical chair of claim 12, wherein said support arm is attached to said mounting support using the ball-joint mechanism.

15. The medical chair of claim 14, wherein said ball-joint mechanism has the ball within a cup inside a housing.

16. The medical chair of claim 15, wherein said cup is formed by a compression cap having a cap seat and by a housing seat, wherein said cap seat and said housing seat are concave.

17. The medical chair of claim 16, wherein said compression cap and said housing are threaded to form a cap screw assembly.

18. The medical chair of claim 17, wherein said ball connects to the rod that passes through said compression cap, said rod connecting to said mounting support;

wherein said compression cap has a conically shaped opening that receives said rod;

wherein when said cap-screw assembly is loose said rod can pivot and rotate; and wherein when said cap-screw assembly is tightened said rod is locked in position.

19. The medical chair of claim 16, wherein said compression cap has a knurled surface.

20. The medical chair of claim 16, wherein medial chair includes a back rest attached to said medical support system.

* * * * *